United States Patent [19]

Homma et al.

[11] 4,381,259
[45] Apr. 26, 1983

[54] SHAMPOO COMPOSITION EMPLOYING ANIONIC PHOSPHORIC ACID ESTER SURFACTANT AND CATIONIC POLYMER

[75] Inventors: Itomi Homma; Noriko Okada, both of Funabashi, Japan

[73] Assignee: Kao Soap Co., Ltd., Tokyo, Japan

[21] Appl. No.: 208,466

[22] Filed: Nov. 19, 1980

[30] Foreign Application Priority Data

Dec. 28, 1979 [JP] Japan ................. 54/173440

[51] Int. Cl.³ .................. C11D 3/36; C11D 1/14
[52] U.S. Cl. .................... 252/542; 252/545; 252/546; 252/547; 252/548; 252/550; 252/551; 252/174.16; 252/174.23; 252/DIG. 2; 252/DIG. 13; 424/70; 424/78
[58] Field of Search ............ 252/174.16, 174.23, 252/545, DIG. 2, DIG. 3, DIG. 13, 548, 550, 547, 551, 542, 546; 424/70, 78

[56] References Cited

U.S. PATENT DOCUMENTS

| | | | |
|---|---|---|---|
| 3,980,769 | 9/1976 | Ghilardi et al. | 424/70 |
| 3,996,146 | 12/1976 | Tarasov et al. | 252/142 |
| 4,075,131 | 2/1978 | Sterling | 252/542 |
| 4,080,310 | 3/1978 | Ng et al. | 252/544 |
| 4,132,679 | 1/1979 | Tsutsumi et al. | 252/545 |
| 4,259,204 | 3/1981 | Homma | 252/174.16 |
| 4,273,760 | 6/1981 | Koehler et al. | 424/70 |
| 4,298,494 | 11/1981 | Parslow et al. | 252/174.16 |

FOREIGN PATENT DOCUMENTS 54-134712 10/1979 Japan .
1443426 7/1976 United Kingdom .

Primary Examiner—P. E. Willis, Jr.
Attorney, Agent, or Firm—Flynn, Thiel, Boutell & Tanis

[57] ABSTRACT

A liquid hair shampoo which comprises a shampoo base of surfactant effective for washing hair, 0.1 to 2.5 wt. % of anionic phosphoric acid ester surface active agent and 0.05 to 2.5 wt. % of a cationic polymer effective for conditioning hair.

9 Claims, No Drawings

SHAMPOO COMPOSITION EMPLOYING ANIONIC PHOSPHORIC ACID ESTER SURFACTANT AND CATIONIC POLYMER

The present invention relates to a hair shampoo composition. More particularly, the present invention relates to a shampoo composition which imparts excellent combing and brushing properties to hair washed therewith and which comprises a shampoo base containing anionic phosphoric acid ester surface active agent and cationic polymer.

In conventional shampoo compositions, one or a mixture of two or more of anionic surface active agents such as alkylsulfates and polyoxyethylene alkylsulfates; nonionic surface active agents such as polyoxyethylene alkyl ethers and fatty acid alkylolamides; and amphoteric surface active agents such as alkylbetaines and alkylamine oxides, have been used as a shampoo base. However, if shampoo compositions containing those shampoo bases are used, the washed hair has an undesirable touch or feel, generally called "creak", after the hair is shampooed and then rinsed with water. This causes a poor brushing property of incompletely dried hair, for example, hair which has been dried with a towel. Further, after complete drying, the hair cannot be set well, its combing or brushing property is poor, and it has undesirable electrostatic properties when brushed in a low humidity atmosphere so as to cause the hair to "fly", thereby making the brushing property poorer. The poor combing or brushing property of hair immediately after shampooing or during trimming treatments effected thereafter causes damage of hair, such as split hairs or breakage thereof. Finally, the natural lustre and resiliency of the hair is damaged. In view of these circumstances, an improvement of shampoo compositions has eagerly been desired.

After intensive investigations for the purpose of overcoming those defects of the conventional shampoo compositions, the inventor has discovered, unexpectedly in view of the prior art, that a shampoo composition capable of imparting an excellent combing or brushing property to hair can be obtained by incorporating:

(a) 0.1–2.5 wt. %, based on the total weight of the shampoo composition, of one or a mixture of two or more anionic phosphoric acid ester surface active agents of the formula (1):

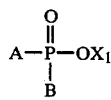

wherein A is

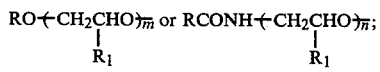

R is linear or branched alkyl having an average carbon atom number of from 8 to 18 or linear or branched alkenyl having an average carbon atom number of from 8 to 18; $R_1$ is hydrogen or methyl; m is from 0 to 8; n is from 1 to 8; B is —$OX_2$ or —A; and $X_1$ and $X_2$, which can be the same or different, are hydrogen, alkali metal, alkyl ($C_1$–$C_3$)-substituted ammonium or hydroxyalkyl ($C_1$–$C_3$)-substituted ammonium;

(b) 0.05–2.5 wt. %, based on the total weight of the shampoo composition, of a cationic polymer, in a conventional shampoo base selected from the group consisting of anionic surface active agents, nonionic surface active agents, amphoteric surface active agents and mixtures thereof.

As the anionic surface active agents, nonionic surface active agents and amphoteric surface active agents, used as the shampoo base in the present invention, the following compounds can be mentioned:

(i) Anionic surface active agents:

Straight chain or branched alkylbenzenesulfonates having an alkyl group of 10–16 carbon atoms on the average in the molecule, Alkyl or alkenylethoxysulfates having a straight chain or branched alkyl group or alkenyl group of 8–20 carbon atoms on the average, to which has been adducted 0.5–8 moles of ethylene oxide, on the average, per molecule, Alkyl or alkenylsulfates having an alkyl or alkenyl group of 10–20 carbon atoms on the average in the molecule, Olefinsulfonates containing 10–20 carbon atoms on the average in the molecule, Alkanesulfonates containing 10–20 carbon atoms on the average in the molecule, Saturated or unsaturated fatty acid salts containing 10–20 carbon atoms on the average in the molecule, Alkyl or alkenylethoxycarbonates having an alkyl or alkenyl group of 10–20 carbon atoms on the average to which has been adducted 0.5–8 moles of ethylene oxide on the average, per molecule, and α-Sulfofatty acid salts or esters of the formula:

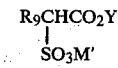

wherein Y represents an alkyl group of 1–3 carbon atoms or a counter ion, M' represents a counter ion and $R_9$ represents an alkyl or alkenyl group containing 10–20 carbon atoms.

As the counter ions of the anionic surface active agents, there can be mentioned alkali metal ions such as sodium and potassium, alkaline earth metal ions such as calcium and magnesium, ammonium ion and alkanolamines having 1–3 alkanol groups of 2–3 carbon atoms (such as monoethanolamine, diethanolamine, triethanolamine and triisopropanolamine).

(ii) Nonionic surface active agents:

Polyoxyethylenealkyl or alkenyl ethers having a primary or secondary alkyl group or alkenyl group of 8–20 carbon atoms, on the average, to which 3–12 moles of ethylene oxide have been added, per molecule.

Polyoxyethylene alkylphenyl ethers having an alkyl group of 8–12 carbon atoms, on the average, to which 3–12 moles of ethylene oxide have been added, per molecule, and Higher fatty acid alkanolamides or alkylene oxide adducts thereof of the formula:

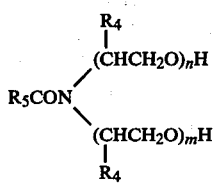

wherein $R_4$ represents H or $CH_3$, $R_5$ represents an alkyl or alkenyl group containing 10–20 carbon atoms, n represents an integer of 1–3 and m represents an integer of 0–3.

(iii) Amphoteric surface active agents:
Alkylamine oxides of the formula:

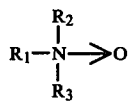

wherein $R_1$ represents an alkyl or alkenyl group of 10–20 carbon atoms, and $R_2$ and $R_3$ each represent an alkyl group of 1–3 carbon atoms, $R_2$ and $R_3$ being the same as or different from each other, Alkylbetaines or sulfobetaines of the formula:

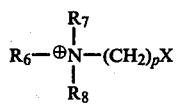

wherein $R_6$ represents an alkyl or alkenyl group having 10–20 carbon atoms, $R_7$ and $R_8$ each represent an alkyl group of 1–4 carbon atoms, p represents an integer of 1–3 and X represents $-COO^\ominus$ or $-SO_3^\ominus$ group, Imidazoline-type amphoteric surface active agents of the formula:

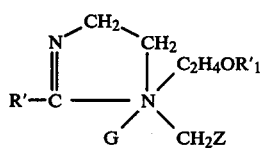

wherein R' represents a fatty acid radical of 10–20 carbon atoms on the average, $R'_1$ represents H, Na or $CH_2COOMe$, Z represents COOMe, $CH_2COOMe$ or

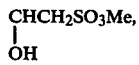

Me being Na, H or an organic base, G represents OH, an acidic salt or an anionic surfactant sulfuric acid salt or a sulfated compound.

Among the above-described shampoo bases, particularly preferred shampoo bases are anionic surface active agents such as straight chain alkylsulfates containing 10–14 carbon atoms on the average and polyoxyethylene alkylsulfates having an alkyl group of 8–20 carbon atoms on the average, higher fatty acid mono-or dialkanolamides having an alkyl group of 10–14 carbon atoms on the average, alkylamine oxides having the same carbon atom number range as described for them above, alkylbetaines and imidazoline-type amphoteric surface active agents.

The anionic phosphoric acid ester surface active agents used in the present invention are shown by general formula (1) given above. As the alkali metals, for X in general formula (1), there can be mentioned, for example, lithium, potassium and sodium. The alkyl-substituted ammonium or hydroxyalkyl-substituted ammonium, for X in formula (1), are formed by quaternizing amines, which have been used for neutralizing phosphoric acid in the step of preparing the anionic phosphoric acid ester salt of general formula (1), into corresponding cations after the neutralization step. The corresponding amines are primary, secondary and tertiary amines having an alkyl group of 1–3 carbon atoms or hydroxyl-containing, corresponding alkyl groups. As examples of them, there can be mentioned dimethylmonoethanolamine, methyldiethanolamine, trimethylamine, triethylamine, dipropylamine, propyldimethylamine, monoethanolamine, diethanolamine, triethanolamine, isopropyldimethylamine and isopropylethanolamine. Preferred amines are monoethanolamine, diethanolamine and triethanolamine. Among them, triethanolamine is particularly preferred.

As preferred examples of the anionic phosphoric acid ester surface active agents according to the present invention, there can be mentioned mono- and di-alkyl or alkenyl (12–18 carbon atoms; the same shall apply thereinafter) phosphate Na or triethanolamine (TEA) salts, mono- or di-polyoxyethylene ($\overline{P}=1-5$) alkyl or alkenyl ether phosphate Na or TEA salts and mono- or di-polyoxypropylene ($\overline{P}=1-5$) alkyl or alkenyl ether phosphate Na or TEA salts, as well as mixtures of them.

As the cationic polymers used in the present invention, the following polymers can be mentioned:

(i) Copolymers of quaternized vinylpyrrolidone and aminoethyl methacrylate (such as GAF Coat 755; a product of GAF CO.), (ii) Copolymers of adipic acid and dimethylaminohydroxypropylene diethylenetriamine (such as Carteretin F4; a product of SANDOZ Co.), (iii) Poly-(N,N-dimethyl-3,5-methylenepiperidinium chloride) (such as Merquat 100; a product of MERCK Co.), (iv) Copolymers of N,N-dimethyl-3,5-methylenepiperidinium chloride and acrylamide (such as Merquat 550; a product of MERCK Co.), (v) Copolymers of acrylamide and B-methacryloxyethyltrimethyl ammonium (such as Reten 220; a product of Hercules Co.), (vi) Quaternized guar gum (such as Jaguar C-13; a product of MEYHALL Co.), (vii) Polyethyleneimines (such as Epomin P-100; a product of Nihon Shokubai Kogyo Co.), (viii) Cationized cellulose (such as Polymer JR-400; a product of UCC Co.), and (ix) Condensates of polyamines and polyglycols (such as Polycoat H; a product of HENKEL Co.).

Among them, poly-(N,N-dimethyl-3,5-methylenepiperidinium chloride), copolymers of N,N-dimethyl-3,5-methylenepiperidinium chloride and acrylamide, and cationized cellulose are particularly preferred.

One or a mixture of two or more of the anionic surface active agents, nonionic surface active agents and amphoteric surface active agents, which are essential, principal, surface active agent ingredients of the shampoo compositions of the present invention, should be incorporated in the shampoo composition in a total amount of 1–30 wt. %. For improving the combing or brushing property, the anionic phosphoric acid ester surface active agent is used in an amount of 0.1–2.5 wt. %, preferably 0.5–2.0 wt. %, and the cationic polymer is used in an amount of 0.05–2.5 wt. %, preferably 0.1–2 wt. %.

For practical use, the composition of the present invention must be in the form of an aqueous paste or liquid having a pH of 4–8.

The shampoo composition of the present invention can contain, in addition to the above-mentioned critical components, conventional adjunct components of shampoo compositions such as solubilizers, for example, propylene glycol, glycerol and urea, viscosity modifiers such as ethanol, inorganic salts, higher alcohols, hydroxyethyl cellulose and hydroxypropyl cellulose, as well as perfumes, coloring matters, ultraviolet light absorbents, antioxidants, dandruff removers, germicides and antiseptics.

The following examples further illustrate the present invention. The invention is not limited to these examples.

The percentages in the following examples are percentages by weight, unless otherwise stated. The numbers indicate the weight % based on the total composition.

EXAMPLE 1

Shampoo compositions as shown in Table 1-1 were prepared and the effects of the respective critical components were examined. The results are shown in Table 1-2.

TABLE 1-1

| | Sample No. | | | |
|---|---|---|---|---|
| | 1 | 2 | 3 | 4 |
| | (Comparisons) | | | (Invention) |
| Sodium POE (2)*1 lauryl ether sulfate | 15% | 15 | 15 | 15 |
| Lauroyl diethanolamide | 3 | 3 | 3 | 3 |
| Miranol C2MSF Conc*2 | 4 | 4 | 4 | 4 |
| Sodium POE (3) lauryl phosphate*3 | 0 | 1 | 0 | 1 |
| Merquat 550*4 | 0 | 0 | 0.5 | 0.5 |
| Water | Balance | | | |

(The composition was adjusted to pH 7.2 with sodium hydroxide and hydrochloric acid)
(Notes)
*1 POE represents polyoxyethylene.
*2 Imidazoline type amphoteric surface active agent (a product of Miranol Co.).
*3 Monoester/diester = 74/26.
*4 Cationic polymer (a product of Merck Co.).

Items of examination and methods

Combing property (combing easiness):

20 Grams of human hair were fixed at their ends to form a tress of hair. The tress was then moistened with water at 40° C. and then washed with 1 g of the shampoo composition and rinsed. The washing and rinsing were repeated twice. After squeezing, the hair was set in a strain gauge and combed, and the power required to move the comb through the hair was measured. The power is shown, in Table 1-2, as "Power required for combing under moist condition". After drying the hair with a dryer, followed by allowing the same to stand in an air-conditioned room at 25° C. under a relative humidity of 65% overnight, the power required to move the comb through the hair for the combing under dry condition was measured in the same manner as described above.

Hair fly:

The hair-flying phenomenon, due to static electricity buildup on the hair during the measurement of the combing power under dry condition, was visually observed.

The observations are evaluated by the following criteria:

⊚ Hair flying phenomenon was not observed at all.
Δ Some hair flying phenomenon was recognized.
X Hair flying phenomenon was recognized.

Touch of hair:

8 Tresses, which were the same as those used for the measurement of power required for the combing, were moistened with water at 40° C. and then washed with 1 g of the shampoo composition and rinsed. The washing and rinsing were repeated twice. The touch or feel of the hair (1) after partially drying the hair with a towel and (2) after drying the hair in a room overnight were judged by a test panel.

In the functional estimation of the touch, the touches of the respective hair samples were estimated in comparison with hair which had been subjected to the same treatment, using Sample No. 1 composition for washing the hair as the standard for comparison.

(The panel comprised 20 females. The numerical values for "Touch of hair" given in Table 1-2 are averages of the rankings assigned by the members of the test panel.)

Rankings:
1: Far inferior to the standard,
2: Inferior to the standard,
3: Equivalent to the standard,
4: Superior to the standard,
5: Far superior to the standard.

TABLE 1-2

| | Sample No. | | | |
|---|---|---|---|---|
| Items | 4 (Invention) | 1 | 2 | 3 |
| | | (Comparisons) | | |
| Power required for combing under moist condition | 242 g | 535 | 294 | 389 |
| Power required for combing under dry condition | 176 | 403 | 205 | 317 |
| Hair fly | ⊚ | X | Δ | Δ |
| Touch of hair (moist) | 4.8 | standard | 2.3 | 3.2 |
| Touch of hair (dry) | 4.8 | standard | 3.2 | 3.0 |

EXAMPLE 2

In a foaming power test in the shampooing procedure, which is a fundamental property required of shampoo compositions, the foaming properties of them in the presence of soil were examined. The results are shown in Table 2.

Foaming test 0.2 g of lanolin was added as an artificial soil to 100 ml of 5% aqueous solution of the shampoo composition. After reversal stirring (at intervals of 10 seconds) with a flat propeller at 40° C. at 1000 rpm for 300 seconds and allowing the same to stand for 30 seconds, the quantity of the foam was measured.

TABLE 2

| | Sample No. | | | |
| --- | --- | --- | --- | --- |
| | 4 (Invention) | 5 | 6 | 7 |
| | | (Comparisons) | | |
| Sodium POE (2) lauryl ether sulfate | 15% | 15 | 15 | 15 |
| Lauroyl diethanolamide | 3 | 3 | 3 | 3 |
| Miranol C2MSF Conc. | 4 | 4 | 4 | 4 |
| Sodium POE (3) lauryl phosphate | 1 | 5 | 10 | 1 |
| Merquat 550 | 0.5 | 0.5 | 0.5 | 5 |
| Water | Balance | | Balance | |
| Foaming property (ml) | 162 | 81 | 75 | 113 |

EXAMPLE 3

The following shampoo compositions 8, 9 and 10 exhibited excellent effects:

| Composition 8 | |
| --- | --- |
| Miranol CSM SF conc. | 15% |
| Sodium POE (2) lauryl ether sulfate | 3 |
| Tween 20 | 8 |
| Sodium salt of a mixture of monoester/diester = 75/25 of general formula (1) wherein A has an average carbon number of 12.5 and —CH$_2$CHO— represents poly-<br>$\qquad\quad$ \|<br>$\qquad\quad$ R$_1$<br>oxyethylene, 3 moles on the average, namely, m = 3 | 1 |
| Merquat 100 | 0.05 |
| Water | Balance pH 7.3 |

| Composition 9 | |
| --- | --- |
| Sodium POE (2) lauryl ether sulfate | 15% |
| Lauryl trimethylamine oxide | 2 |
| Mixture of monoester/diester = 75/25 of general formula (1) wherein A has an average carbon number of 12.0 and<br>—CH$_2$CHO— represents polyoxypropylene,<br>$\quad$ \|<br>$\quad$ R$_1$<br>3 moles on the average, namely, m = 3 | 1 |
| Epomin P-1000 (polyethyleneimine; a product of Nihon Shokubai Kogyo KK.) | 0.5 |
| Water | Balance pH 7.2 |

| Composition 10 | |
| --- | --- |
| Alkyl (average carbon number: 12.5) sulfate triethanolamine salt | 20% |
| Coconut fatty acid diethanolamide | 6 |
| Sodium POE (3) lauryl phosphate (monoester/diester = 71/29) | 1 |
| Polymer JR 400 (cationized cellulose; a product of UCC Co.) | 1 |
| Water | Balance pH 7.5 |

The embodiments of the invention in which an exclusive property or privilege is claimed are defined as follows:

1. A shampoo composition, consisting essentially of
(A) from 0.1 to 2.5% by weight of at least one anionic phosphoric acid ester having the formula

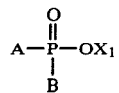

wherein A is

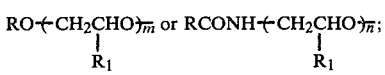

R is alkyl having an average carbon atom number of 8 to 18 or alkenyl having an average carbon atom number of 8 to 18; R$_1$ is hydrogen or methyl; m is from 0 to 8; n is from 1 to 8; B is —OX$_2$ or —A; and X$_1$ and X$_2$, which can be the same or different, are hydrogen, alkali metal, alkyl (C$_1$-C$_3$)-substituted ammonium or hydroxyalkyl (C$_1$-C$_3$)-substituted ammonium;
(B) from 0.05 to 2.5% by weight of at least one cationic polymer effective for conditioning hair selected from the group consisting of
  (i) copolymers of quaternized vinylpyrrolidone and aminoethyl methacrylate,
  (ii) copolymers of adipic acid and dimethylaminohydroxypropylene diethylenetriamine,
  (iii) poly-(N,N-dimethyl-3,5-methylenepiperidinium chloride),
  (iv) copolymers of N,N-dimethyl-3,5-methylenepiperidinium chloride and acrylamide,
  (v) copolymers of acrylamide and β-methacryloxyethyl trimethyl ammonium,
  (vi) polyethyleneimines,
  (vii) cationized cellulose, and
  (viii) condensates of polyamines and polyglycols;
(C) from 1 to 30% by weight of at least one member selected from the group consisting of water-soluble anionic organic surfactant effective for washing hair and different from said anionic phosphoric acid ester, water-soluble nonionic organic surfactant effective for washing hair and water-soluble amphoteric organic surfactant effective for washing hair; and
(D) the balance is essentially water, said shampoo composition having a pH of 4 to 8.

2. A shampoo composition according to claim 1 wherein (C) is selected from the group consisting of straight chain alkylsulfates containing from 10 to 14 carbon atoms on the average, alkylethoxysulfates having alkyl groups of from 8 to 20 carbon atoms on the average added with from 0.5 to 8 moles of ethylene oxide on the average, fatty acid mono- or di-ethanol amides having alkyl groups of from 10 to 14 carbon atoms on the average, alkylamine oxides, alkylbetaines and imidazoline-type amphoteric surface active agents.

3. A shampoo composition according to claim 1 or claim 2 wherein said cationic polymer is selected from the group consisting of poly(N,N-dimethyl-3,5-methylenepiperidinium chloride), copolymers of N,N-dimethyl-3,5-methylenepiperidinium chloride and acrylamide, and cationized cellulose.

4. A shampoo composition as claimed in claim 1 containing from 0.5 to 2.0 wt. % of A and from 0.1 to 2 wt. % of B.

5. A shampoo composition according to claim 1, wherein A is

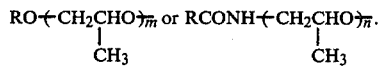

6. A shampoo composition according to claim 1, wherein A is

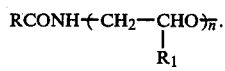

7. A shampoo composition according to claim 1, wherein said cationic polymer consists of poly-(N,N-3,5-methylenepiperidinium chloride).

8. A shampoo composition according to claim 7, wherein said cationic polymer consists of copolymer of N,N-dimethyl-3,5-methylenepiperidinium chloride and acrylamide.

9. A shampoo composition as claimed in claim 1, consisting essentially of about 15% by weight of sodium polyoxyethylene (2) lauryl ether sulfate, about 3% by weight of lauroyl diethanolamide, about 4% by weight of imidazoline amphoteric surfactant, about 1% by weight of sodium polyoxyethylene (3) lauryl phosphate, about 0.5% by weight of copolymer of N,N-dimethyl-3,5-methylenepiperidinium chloride and acrylamide, and the balance is essentially water, said shampoo composition having a pH of 4 to 8.

* * * * *